(12) United States Patent
Genkin et al.

(10) Patent No.: US 8,710,012 B2
(45) Date of Patent: *Apr. 29, 2014

(54) METHOD FOR TREATING ONCOLOGICAL DISEASES

(75) Inventors: Dmitry Dmitrievich Genkin, Saint-Petersburg (RU); Georgy Viktorovich Tets, Saint-Petersburg (RU); Viktor Veniaminovich Tets, Saint-Petersburg (RU)

(73) Assignee: CLS Therapeutics Limited, Guernsey, Channel Islands (GB)

( * ) Notice: Subject to any disclaimer, the term of this patent is extended or adjusted under 35 U.S.C. 154(b) by 617 days.

This patent is subject to a terminal disclaimer.

(21) Appl. No.: 12/708,914

(22) Filed: Feb. 19, 2010

(65) Prior Publication Data

US 2010/0150903 A1   Jun. 17, 2010
US 2013/0209443 A9   Aug. 15, 2013

Related U.S. Application Data

(63) Continuation-in-part of application No. 10/564,609, filed as application No. PCT/RU2004/000260 on Jul. 1, 2004, now abandoned, application No. 12/708,914, which is a continuation-in-part of application No. 11/919,141, filed as application No. PCT/RU2005/000236 on Apr. 25, 2005.

(30) Foreign Application Priority Data

Jul. 14, 2003 (WO) ............... PCT/RU03/00304

(51) Int. Cl.
*A61K 38/43* (2006.01)

(52) U.S. Cl.
USPC ........................................ 514/19.3; 435/196

(58) Field of Classification Search
CPC .................. C12Y 301/21001; A61K 38/465
See application file for complete search history.

(56) References Cited

U.S. PATENT DOCUMENTS

| | | | |
|---|---|---|---|
| 4,485,095 A | 11/1984 | Fujisaki et al. | |
| 5,484,589 A | 1/1996 | Salganik | |
| 5,656,589 A | 8/1997 | Stossel et al. | |
| 5,889,153 A | 3/1999 | Suzuki et al. | |
| 5,952,170 A | 9/1999 | Stroun | |
| 6,033,846 A | 3/2000 | Fournie | |
| 6,156,504 A | 12/2000 | Gocke et al. | |
| 6,391,607 B1 | 5/2002 | Lazar et al. | |
| 6,428,785 B1 | 8/2002 | Gokeen | |
| 6,455,250 B1 | 9/2002 | Aguilera et al. | |
| 6,465,177 B1 | 10/2002 | Hoon | |
| 6,521,409 B1 | 2/2003 | Gocke et al. | |
| 7,612,032 B2 | 11/2009 | Genkin et al. | |
| 2003/0044403 A1 | 3/2003 | Shak | |
| 2004/0001817 A1 | 1/2004 | Giampapa | |
| 2004/0157239 A1 | 8/2004 | Tanuma et al. | |
| 2006/0228347 A1* | 10/2006 | Sunaga et al. | 424/94.6 |
| 2006/0233780 A1 | 10/2006 | Genkin et al. | |
| 2007/0104702 A1 | 5/2007 | Genkin et al. | |
| 2008/0004561 A1 | 1/2008 | Genkin et al. | |
| 2009/0047272 A1 | 2/2009 | Appelbaum et al. | |
| 2009/0053200 A1 | 2/2009 | Genkin et al. | |
| 2010/0061971 A1 | 3/2010 | Genkin et al. | |
| 2010/0150903 A1 | 6/2010 | Genkin et al. | |
| 2010/0303796 A1 | 12/2010 | Genkin et al. | |
| 2011/0033438 A1 | 2/2011 | Bartoov et al. | |
| 2011/0070201 A1 | 3/2011 | Shaaltiel et al. | |
| 2011/0189156 A1 | 8/2011 | Genkin et al. | |

FOREIGN PATENT DOCUMENTS

| | | |
|---|---|---|
| CA | 2394856 | 6/2001 |
| CA | 2184582 | 12/2001 |
| DE | 4024530 | 2/1992 |
| DE | 10221194 | 12/2003 |
| EP | 0325191 | 7/1989 |
| EP | 1666055 | 2/2005 |
| EP | 1655036 | 5/2006 |
| EP | 1661579 | 5/2006 |
| EP | 1880733 | 1/2008 |
| EP | 2095825 | 9/2009 |
| GB | 984464 | 2/1965 |
| GB | 1005985 | 9/1965 |
| JP | 61293927 | 12/1986 |
| JP | 2006-290769 | 10/2006 |
| NZ | 299257 | 8/2000 |
| RU | 2099080 | 12/1997 |
| RU | 2001129826 | 11/2001 |
| RU | 2001104426 | 1/2003 |
| RU | 2202109 | 4/2003 |
| RU | 2207876 | 7/2003 |
| RU | 2003127898 | 9/2003 |

(Continued)

OTHER PUBLICATIONS

Aung et al., Current status and future potential of somatic mutation testing from circulating free DNA in patients with solid tumours, Hugo J, vol. 4, pp. 11-21, 2010.
Boyko et al., Cell-free DNA—a marker to predict ischemic brain damage in a rat stroke experimental model, Journal of Neurosurgical Anesthesiology, vol. 23, pp. 222-228, 2011.
Deocharan B., et al., Alpha-actinin is a cross-reactive renal target for pathogenic anti-DNA antibodies, J. Immunol., vol. 168, pp. 3072-3078, 2002.
Department of Health and Human Services Food and Drug Administration, Federal Register, Dec. 13, 1985, vol. 50, No. 240.
Gormally et al., Circulating free DNA in plasma or serum as biomarker of carcinogenesis: Practical aspects and biological significance, Mutation Research, vol. 635, pp. 105-117, 2007.
Gorrini, C., et al., Effect of apoptogenic stimuli on colon carcinoma cell lines with a different c-myc expression level, Int J Mol Med, vol. 11, pp. 737-742, 2003.
Huttunen, R., et al., Fatal Outcome in Bacteremia is Characterized by High Plasma Cell Free DNA Concentration and Apoptotoc DNA Fragmentation: A Prospective Cohort Study, PLoS ONE, vol. 6, e21700, 2011.

(Continued)

*Primary Examiner* — Christina Bradley
(74) *Attorney, Agent, or Firm* — Troutman Sanders LLP

(57) ABSTRACT

A method to treat cancer and other malignant diseases, said method comprising parenterally administering an agent which destroys blood extracellular DNA into the systemic circulation of a cancer patient to slow down cancer growth. The agent is embodied in the form of a DNase enzyme and, more particularly, as a DNase I enzyme. Doses from 50,000-250,000,000 Kunitz units/day are administered for 5-360 days.

4 Claims, No Drawings

(56) References Cited

FOREIGN PATENT DOCUMENTS

| | | |
|---|---|---|
| RU | 2239404 | 11/2004 |
| RU | 2239442 | 11/2004 |
| RU | 2004108060 | 9/2005 |
| RU | 2267329 | 1/2006 |
| RU | 2269356 | 2/2006 |
| RU | 2269357 | 2/2006 |
| RU | 2269358 | 2/2006 |
| RU | 2269359 | 2/2006 |
| RU | 2308968 | 10/2007 |
| WO | WO93/03709 | 3/1993 |
| WO | WO95/00170 | 1/1995 |
| WO | WO97/28266 | 8/1997 |
| WO | WO97/47751 | 12/1997 |
| WO | WO00/03709 | 1/2000 |
| WO | WO00/31238 | 6/2000 |
| WO | WO01/74905 | 10/2001 |
| WO | WO03/068254 | 8/2003 |
| WO | WO2005/004789 | 1/2005 |
| WO | WO2005/007187 | 1/2005 |
| WO | WO2005004903 | 1/2005 |
| WO | WO2005004904 | 1/2005 |
| WO | WO2005/115444 | 12/2005 |
| WO | WO2006/130034 | 12/2006 |
| WO | WO2008047364 | 4/2008 |
| WO | WO2008/066403 | 6/2008 |
| WO | WO2011/073665 | 6/2011 |
| WO | WO2012/075506 | 6/2012 |

OTHER PUBLICATIONS

International Search Report for PCT/RU2004/000262, mailed on Oct. 21, 2004.

International Search Report for PCT/RU2006/000642, mailed on Aug. 2, 2007.

Jylhava et al., Aging is associated with quantitative and qualitative changes in circulating cell-free DNA: the Vitality 90+ study, Mechanisms of Ageing and Development, vol. 132, pp. 20-26, 2011.

Lachmann PJ, Lupus and Desoxyribonuclease, Lupus, vol. 12, pp. 202-206, 2003.

Lecompte, et al., Detection of free-circulating tumor-associated DNA in plasma of colorectal cancer patients and its association with prognosis, Int. J. Cancer, vol. 100, pp. 542-548, 2002.

Lee, D., Continued Marketing of a Useless Drug ('Varidase') in Panama, Lancet, Mar., vol. 335, p. 667, 1990.

Leon et al., Free DNA in the Serum of Cancer Patients and the Effect of Therapy, Cancer Research, vol. 37, pp. 646-650, 1977.

Li et al., The *Haemophilus ducreyi* cytolethal distending toxin activates sensors of DNA damage and repair complexes in proliferating and non-proliferating cells, Cellular Microbiology, vol. 4, pp. 87-99, 2002.

Liggett et al. , Methylation patterns of cell-free plasma DNA in relapsing-remitting multiple sclerosis, Journal of Neurological Sciences, vol. 290, pp. 16-21, 2010.

Maurer, HR, Bromelain: biochemistry, pharmacology and medical use, Cell Mol. Life. Sci., vol. 58, pp. 1234-1245, 2001.

Merkus et al., DNase treatment for atelectasis in infants with severe respiratory syncytial virus bronchiolitis, Eur Respir J, vol. 18, pp. 734-737, 2001.

Moreira VG et al., Usefulness of cell-free plasma DNA, procalcitonin and C-reactive protein as markers of infection in febrile patients, Annals of Clinical Biochemistry, vol. 47, pp. 253-258, 2010.

Mosca et al., Cell-free DNA in the plasma of patients with systemic sclerosis, Clinical Rheumatology, vol. 28, pp. 1437-1440, 2009.

Oliven et al., Orally and Rectally Administered Streptokinase, Pharmacology, vol. 22, pp. 135-138, 1981.

Pisetsky, D., Immune response to DNA in systemic lupus erythematosus, Isr. Med. Assoc. J., vol. 3, pp. 850-853, 2001.

Pressler T., Review of recombinant human deoxyribonuclease (rhDNase) in the management of patients with cystic fibrosis, Biologics: Targets & Therapy, vol. 2, pp. 611-617, 2008.

Pulmozyme® (dornase alfa) Inhalation Solution product leaflet, Genetech, Inc., 2005.

Rao KS and Shrivastaw KP, Studies on the synthesis and degradation of DNA in developing and old chick cerebellum, Journal of Neurochemistry, vol. 27, pp. 1205-1210, 1976.

Sherry et al., Presence and Significance of Desoxyribose Nucleoprotein in the Purulent Pleural Exudates of Patients, Proc, Soc. Exp. Biol. Med., pp. 179-184, 1948.

Shimony et al., Cell free DNA detected by a novel method in acute ST-elevation myocardial infarction patients, Acute Cardiac Care, vol. 12, pp. 109-111, 2010.

Simpson G., et al., Successful treatment of empyema thoracis with human recombinant deoxyribonuclease, Thorax, vol. 58, pp. 365-366, 2003.

Supplementary European Search Report for European Patent Appl. No. EP06843990, dated Nov. 23, 2009 and cf Form 1507.

Supplementary European Search Report for European Patent Appl. No. EP04748955, mailed May 19, 2009.

Supplementary European Search Report for European Patent Appl. No. EP04775224, mailed Oct. 28, 2009.

Supplementary European Search Report for European Patent Appl. No. EP05745412, dated Jul. 10, 2009.

Supplementary European Search Report for European Patent Appl. No. EP03796243, dated Jan. 12, 2010.

Tetz, GV, et al., Effect of DNase and Antibiotics on Biofilm Characteristics, Antimicrobial Agents and Chemotherapy, vol. 53, pp. 1204-1209, 2009.

Tetz VV and Tetz GV, Effect of Extracellular DNA Destruction by DNase I on Characteristics of Forming Biofilms, DNA and Cell Biology, vol. 29, pp. 399-405, 2010.

Tetz, GV, et al., Effect of nucleolytic, proteolytic, and lipolytic enzymes on transfer of antibiotic resistance genes in mixed bacterial communities, Universal Journal of Medicine and Dentistry, vol. 1, pp. 46-50, 2012.

Translation of International Preliminary Report on Patentability for PCT/RU2004/000262, mailed Apr. 12, 2006.

Translation of International Preliminary Report on Patentability for PCT/RU2006/000642, dated Jul. 7, 2009.

Ye et al., Quantification of Circulating Cell-Free DNA in the Serum of Patients with Obstructive Sleep Apnea-Hypopnea Syndrome, Lung, vol. 188, pp. 469-474, 2010.

Varidase product information from EPGOnline, accessed on Dec. 12, 2011.

Vonmoos, P.L. and Straub, P.W., Absorption and hematologic effect of streptokinase-streptodornase (varidase) after intracavital or oral administration, Schweiz Med Wochenschr, vol. 109, pp. 1538-1544,1979, Abstract.

Whitchurch, et al., Extracellular DNA Required for Bacterial Biofilm Formation, Science, vol. 295, p. 1487, 2002.

Zaman, et al., Direct amplification of Entamoeba histolytica DNA from amoebic liver abscess pus using polymerase chain reaction, Parasitol. Res., vol. 86, pp. 724-728, 2000.

Zaravinos et al., Levosimendan reduces plasma cell-free DNA levels in patients with ischemic cardiomyopathy, J. Thromb. Thrombolysis, vol. 31, pp. 180-187, 2011.

Botto, N., et al., Elevated levels of oxidative DNA damage in patients with coronary artery disease, Coronary Artery Disease, vol. 13, pp. 269-274, 2002.

Davis JC et al., Recombinant human Dnase I (rhDNase) in patients with lupus nephritis, Lupus, vol. 8, pp. 68-76, 1999.

Dayan, Pharmacological-Toxicological (Expert Report on Recombinant Human Deoxyribonuclease I (rhDNase; Pulmozyme™) , Hum. Exp. Toxicol., 13: S2, 1994.

Extended European Search Report for European Patent Appl. No. EP12170750 dated Aug. 3, 2012.

Extended European Search Report for European Patent Appl. No. EP12170754 dated Aug. 3, 2012.

Extended European Search Report for European Patent Appl. No. EP12170757 dated Aug. 3, 2012.

Favorov, P.V. Issledovaniye kinetiki prevrashchenii DNK pod deistviem DNK-topoizomeraz i DNK-abzimov, author's abstract of PhD thesis in biological sciences, M., pp. 3-4, 1999 (Reference in Russian and English-language translation).

Funakoshi, A, et al., Clinical Investigation of Serum Deoxyribonuclease: II. Clinical Studies of Serum

(56) References Cited

OTHER PUBLICATIONS

Deoxyribonuclease Activity in Pancreatic Disease, Gastroenterologia Japonica, vol. 14, pp. 436-440, 1979.
Gluhov BM, Znachenije nukleaz v patogeneze neirovirusnyh zabolevanij, Avtoreferat dissertatsii na soiskanie uchenoi stepeni doktora medicinskikh nauk (author's abstract of MD thesis in medical sciences), Novosibirsk, pp. 15-16, 21-26, 1996 (Reference in Russian and English-language translation of pp. 14-17 and 20-27).
Kalandarishvili F., Nakoplenie spontanno povrezhdennoj DNK v nei postgepatjektomirovannoj pecheni u staryh krys, Med. Novosti Gruzii, No. 5, pp. 11-12, 1998 (Reference in Russian and English-language translation).
Kaprin et al., Prognoz i lechenie bol'nih poverhnostnim rakom mochevogo puziria visokoi stepeni riska, Visokie Tehnologii v Onkologii, Rostov-na-Donu, vol. 3, pp. 149-150, 2000 (Reference in Russian and English-language translation).
Mel'Nikov D, et al., Voprosy onkologicheskoi pomoschi na etape reformirovaniya zdravookhraneniya, Ekaterinburg, pp. 159-161, 1996 (Reference in Russian and English-language translation).
Nikolenko G. N., Sozdanie rekombinantnykh antitel 17 protiv virusa kleschevogo entsefalita i izuchenie ikh svoystv, Avtoreferat dissertatsii na soiskanie uchenoi stepeni kandidata biologicheskikh nauk (author's abstract of PhD thesis in biological sciences), Koltsovo, pp. 1-2, 19, 1999 (Reference in Russian and English-language translation).
Osivac et al., Reorganizacija DNK i biologicheskoje starenije, Biohimija, vol. 62, pp. 1491-1502, 1997 (Reference in Russian and English-language translation).
Perel'Man Mi, et al., Molekuljarnaja medicina i lechenie tuberkuleza, Problemi tuberkuleza, No. 5, pp. 5-7, 2001 (Reference in Russian and English-language translation).
Yastrebova N.E., Razrabotka i izuchenie diagnosticheskikh vozmozhnostei immunofermentnykh test-sistem na osnove antigennykh preparatov zolotistogo stafilokokka i DNK, Avtoreferat dissertatsii na soiskanie uchenoi stepeni kandidata meditsinskikh nauk (author's abstract of PhD thesis in medical sciences), M., pp. 17-18, 1988 (Reference in Russian and English-language translation).
Amendment filed in U.S. Appl. No. 10/564,861 dated Jun. 24, 2008.
Anker, P. and Stroun, M., Tumor-related alterations in circulating DNA, potential for diagnosis, prognosis and detection of minimal residual disease, Leukemia, vol. 15, pp. 289-291, 2001.
Ashton, Growing pains for biopharmaceuticals, Nature Biotech, 19, 307-311, 2001.
Biologia Stareniya, rukovodstvo po fiziologii, pod ped. N.I. Arinchina et al. L., Nauka, pp. 280-282, 1982.
Burt, et al., Detection of circulating donor deoxyribonucleic acid by microsatellite analysis in a liver transplant recipient, Liver Transpl Surg., vol. 2(5), pp. 391-394, 1996.
Davis, Brian R, et al., Somatic mosaicism in the Wiskotl-Aldrich syndrome: Molecular and functional characterization of genotypic revertants, Clinical Immunology, vol. 135, pp. 72-83, 2010.
Dittmar, Manuela et al., A novel mutation in the *DNASE* gene is related with protein instability and decreased enzyme activity in thyroid autoimmunity, Journal of Autoimmunity, vol. 32, pp. 7-13, 2009.
El Hassan NO, et al. Rescue use of Dnase in critical lung atelectas mucus retention in premature neonates. Pediatrics, vol. 108, pp. 468-470, 2001.
Erickson, Robert P., Somatic gene mutation and human disease other than cancer, Mutation Research, vol. 543, pp. 125-136,2003.
Erickson, Robert P., Somatic gene mutation and human disease other than cancer: An update, Mutation Research, vol. 705, pp. 96-106, 2010.
Freshney, R. I., Culture of Animal Cells, A Manual of Basic Technique, Alan R. Liss, Inc., New York, pp. 3-4, 1983.
Gannushikina, I.V., et al., Plasma DNA Levels in Patients with Atherosclerotic Involvement of the Major Arteries of the Head and lateral Amyotrophic Sclerosis, Bulletin of Experimental Biology andMedicine, vol. 124, No. 12, pp. 1164-1166, 1997 (Translated from: Gannushikina IV. et al., Uroven DNK v plazme krovi bolnykh aterosklerotischeskim porazheniem magistralnykh artery golovy i bokovym amiotroficheskim sklerozom, Byulleten' Experimental'noi Biologii i Meditsiny, Moscow, Meditsina, No. 12, pp. 610-612,1997).
Gibbs, et al., Mechanism-Based Target Identification and Drug Discovery in Cancer Research, Science, vol. 287, pp. 1969-1973, 2000.
Gura, Systems for Identifying New Drugs Are Often Faulty, Science, vol. 278, pp. 1041-1042, 1997.
Hann, et al. Building 'validated' mouse models of human cancer. Curr Opin Cell Biol, vol. 13, pp. 778-784, 2001.
Holterhus, Paul-Martin, et al., Mosaicism due to a Somatic Mutation of the Androgen Receptor Gene Determines Phenotype in Androgen Insensitivity Syndrome, Journal of Clinical Endocrinology and Metabolism, vol. 82, No. 11, pp. 3584-3589, 1997.
Horlitz, Martin et al., Optimized Quantification of Fragmented, Free Circulating DNA in Human Blood Plasma Using a Calibrated Duplex Real-Time PCR, PLoS ONE, vol. 4, Issue 9, e7207, 2009.
Hursting, Stephen D. et al. Calorie Restriction, Aging and Cancer Prevention: Mechanisms of Action and Applicability to Humans, Annual Review of Medicine, vol. 54, pp. 131-152, 2003.
International Search Report for PCT/RU2004/000261, mailed on Oct. 21, 2004.
International Search Report for PCT/RU2005/000236, mailed on Nov. 24, 2005.
International Search Report for PCT/RU2003/000304, mailed on Mar. 25, 2004.
International Search Report for PCT/RU2004/000260, mailed on Dec. 9, 2004.
Juncosa, DNA on the Loose: Next-Gen Blood Tests Tap Free-Floating Genetic Material, Scientific American, Features, Mar. 18, 2009.
Kagan, Valerian E. et al., Toward Mechanism-based Antioxidant Interventions, Ann NY Acad Sci., vol. 959, pp. 188-198, 2002.
Kawane, K, et at, DNAse II deficiency causes chronic polyarthritis in mice, Nature Clinical Practice Rheumatology, vol. 3, No. 4, p. 192, 2007.
Krapf F, et al., The estimation of circulating immune complexes, C3d, and anti-ds-DNA-antibody serum levels in the monitoring of therapeutic plasmapheresis in a patient with systemic lupus erythematosus. A case report, Clin Exp Rheumatol., vol. 3, pp. 159-162, 1985.
Leland et al., Cancer chemotherapy—ribonucleases to the rescue, Chem. & Bio., vol. 8, pp. 405-413, 2001.
Macanovic, et al., The treatment of systemic lupus erythematosus (SLE) in *NZB/W* F 1 hybrid mice; studies with recombinant murine DNase and with dexamethasone. Clinical and Experimental Immunology, vol. 106, pp. 243-252, 1996.
Malickova, Karin, et al., Decreased Activily of DNase-I Predisposes to Immune-Mediated Complications in IBD Patients During Anti-TNFA Treatment, Gastroenterology, Abstract 202, vol. 138 (5 Supplement 1), S-37, 2010.
Mutirangura A., Serum/plasma viral DNA: mechanisms and diagnostic applications to nasopharyngeal an cervical carcinoma., Ann N Y Acad Sci.; 945: 59-67, 2001.
Nestle & Roberts, An extracellular nuclease from *Serratia marcescens*, J. Biol. Chem., 244, 5213-5218, 1969.
Ngan et al., Remarkable Application of Serum EBV EBER-1 in Monitoring Response of Nasopharyngeal Cancer Patients to Salvage Chemotherapy, Ann. NY Acad. Sci., 945, 73-79, 2001.
Translation of PCT International Preliminary Report on Patentability for PCT/RU2005/000236, mailed on Nov. 24, 2005.
Prince, W.S., et al, Pharmacodynamics of recombinant human DNase I in serum, Clin. Exp. Immunol , vol. 113, pp. 289-296, 1998.
Raz E. et al., Anti-DNA antibodies bind directly to renal antigens and induce kidney dysfunction in the isolated perfused rat kidney, J Immunol , vol. 142, pp. 76-82, 1989.
Riches, A.C., et al., Blood Volume Determination in the Mouse, J. Physiol., vol. 228, pp. 279-284, 1973.
Ross, Kenneth Andrew, Evidence for somatic gene conversion and deletion in bipolar disorder, Crohn's disease, coronary artery disease, hypertension, rheumatoid arthritis, type-1 diabetes, and type-2 diabetes, BMC Medicine, 9:12, 2011.
Rowlatt, C., et al., Lifespan, Age Changes and Tumour Incidence in an Ageing C57bl Mouse Colony, Laboratory Animals, vol. 10, pp. 419-442, 1976.

(56) References Cited

OTHER PUBLICATIONS

Schapira, Anthony H. V., Mitochondrial disease, Lancet, vol. 368, pp. 70-82, 2006.

Sergeeva L. M., Kliniko-Iaboratonaya otsenka mukoliticheskogo effekta pulmozima u bolnykh mukovistsidozom, Ekaterinburg, PhD dissertation in medicine, p. 9, paragraphs 2-3; p. 12, paragraph 4; p. 13, paragraphs 1-2; p. 17, paragraph 4; p. 18, paragraph 1; p. 30, paragraphs 3-4; p. 31, paragraph 2, 1999, (Reference in Russian and English Translation).

Shak et al., Recombinant human DNAse I reduces the viscosity of cystic fibrosis sputum, Proc. Natl. Acad. Sci., vol. 87, pp. 9188-9192, 1990.

Shevchuk, N.A., Vremyarazreshenniy Immunofluorescentniy Analiz na DNK i Issledovanie Soderzhaniya DNK v Syvoroike Cheloveka, Voprosi Medicinskoi Khimii, No. 4, 2001 (Reference in Russian and English Translation).

SIGMA Product Information Sheet for Deoxyribonuclease I From Bovine Pancreas.

Sugihara S., et al., Deoxyribonuclease treatment prevents blood-borne liver metastasis of cutaneously transplanted tumour cells in mice, British Journal of Cancer, vol. 67, pp. 66-70, 1993.

Supplementary Partial European Search Report for Application No. EP04748955.4, dated May 19, 2009.

Translation of PCT International Preliminary Report on Patentability for PCT/RU2003/000304, dated Nov. 1, 2005.

Translation PCT International Preliminary Report on Patentability for PCT/RU2004/000261, mailed Dec. 2, 2005.

Translation PCT International Preliminary Report on Patentability for PCT/RU2004/000260, mailed Jan. 14, 2006.

Ulrich & Friend, Toxicogenomics and drug discovery: will new technologies help us produce better drugs? Nature, 1, 84-88, 2002.

Yasuda, Toshihiro et al., Activity Measurement for Deoxyribonucleases I and II with Picogram Sensitivity Based on DNA/SYBR Green I Fluorescence, Analytical Biochemistry, vol. 255, pp. 274-276, 1998.

Zhong, et al., Presence of mitochondrial tRNA(leu(UUR) A to G 3243 mutation in DNA extracted from serum and plasma of patients with type A 2 diabetes mellitus. J. Clin. Pathol., vol. 53(6), pp. 466-469, 2000.

\* cited by examiner

METHOD FOR TREATING ONCOLOGICAL DISEASES

RELATED APPLICATIONS

This application is a continuation-in-part of:
(i) U.S. application Ser. No. 10/564,861, filed on Jan. 12, 2006, now U.S. Pat. No. 7,612,032, issued Nov. 3, 2009, which is a national phase application under 35 U.S.C. §371 of International Patent Application No. PCT/RU2004/00261, filed Jul. 1, 2004 (published in Russian on Jan. 20, 2005 as WO 2005/004903), which claims priority of Russian Federation Patent Application No. RU2004108061, filed Mar. 12, 2004 and International Patent Application No. PCT/RU2003/000304 filed Jul. 14, 2003;
(ii) U.S. application Ser. No. 10/564,609, filed on Jan. 12, 2006, which is a U.S. national phase application under 35 U.S.C. §371 of International Patent Application No. PCT/RU2004/00260, filed Jul. 1, 2004 (published in Russian on Jan. 20, 2005 as WO 2005/004789), which claims priority of Russian Federation Patent Application No. RU2004108057, filed Mar. 12, 2004 and International Patent Application No. PCT/RU2003/000304 filed Jul. 14, 2003; and
(iii) U.S. application Ser. No. 11/919,141, filed on Oct. 23, 2007, which is a U.S. national phase application under 35 U.S.C. §371 of International Patent Application No. PCT/RU2005/000236, filed Apr. 25, 2005 (published in Russian on Dec. 7, 2006 as WO 2006/130034).
The contents of the above applications are incorporated by reference herein as if rewritten in their entirety.

BACKGROUND OF THE INVENTION

1. Field of the Invention

The present invention generally relates to a method for treating oncological diseases by administering an agent that destroys extracellular DNA in the blood of a cancer patient.

2. Description of the Background Art

Populations of tumor cells developing in patients have a very high genetic variability which exceeds a same for healthy cells. Genetic variability of cancer cell populations causes mutated cells to generate phenotypes that (1) are insensitive to immune and morphogenetic control, (2) have an ability to invade and metastasize, and (3) are desensitized to cancer therapies. Selection and clonal expansion of cancer cells are both considered to underlie a biological and a clinical progression of tumors. For this reason, an approach of modern cancer therapies is based on a destruction of cancer cell clones in patients by means of chemotherapy, immunotherapy, biotherapy, surgical methods, or a combination thereof.

Chemotherapy, radiotherapy, biotherapy and more recent immunotherapy are the most commonly used non-surgical methods of treating cancer diseases. These therapies are administered to destruct, to damage or to inactivate a cancer cell's intracellular DNA.

The chemotherapy approach is based on administration of well known compounds: platinum preparations, antracycline antibiotics, alkylating agents and podophyllotoxins. The radioimmunotherapy approach is based on irradiation of intracellular DNA of cancer cells' nuclei. Alpha particles from alpha emitters are specially delivered into the cancerous cells to increase effects on those cells' intracellular DNA. Biotherapeutic and immunotherapeutic approaches are based on an induction of apoptosis of cancer cells, which induces death of the cancer cell. Apoptosis starts with an activation of intracellular nucleuses and follows with a degradation of the tumor cell's intracellular DNA. This process is accomplished, for example, by means of administering genotherapeutic constructions that consist of genes that induce apoptosis or genes coding the factors which activate the nucleuses.

Aguilera. et al. discloses in U.S. Pat. No. 6,455,250 endonuclease Endo SR to treat cancer diseases by mode of its intracellular delivery into target cells. This method and chemotherapy, with Etopozide-4-Demetilpipodophylotoxe (4,6-O—R)-etiliden-b-D-glycopiranozid, were both selected for a prototype of the present invention.

Topoizomeraze II is an essential cell enzyme that regulates many aspects of DNA function. The enzyme is responsible for interconversion of different topological forms of intracellular DNA by means of a generation of transitory breaks of double-stranded DNA. Etopozide, as a Topoizomeraze II inhibitor, increases an intracellular level of "broken DNA-Topoizomeraze II" complexes.

The result of this drug's influence is an accumulation of double-stranded intracellular DNA breaks which lead to the cell's death. A drawback of this method prototype, along with well-known methods, is their low efficacy. These methods imply that mostly the cancer cells' intracellular DNA is the therapeutic target. Because of high genetic variability, these cancer cells become desensitized to the therapies before they are adequately eliminated. A further disadvantage is that the intracellular DNA is a difficult-to-approach target; it leads to necessary high-dosing antineoplastic chemotherapy and/or other complicated delivery systems. A final disadvantage to these methods is that they are highly toxic: their influence on cancerous cells' intracellular DNA also damages healthy cells' DNA.

SUMMARY OF THE INVENTION

An object of this invention is to develop a highly efficient cancer therapy having low toxicity. It is an object to resolve the foregoing drawbacks by administering into systemic circulation an agent which destroys blood extracellular DNA.

The agent is introduced in doses that alter an electrophoretic profile of blood extracellular DNA, which could be detectable by pulse-electrophoresis. Doses of the agent are introduced according to a regime schedule that provides for plasma hydrolytic activity exceeding 150 Kunitz units/liter of blood plasma. This level can be supported for more than 12 hours within a 24 hour period. The treatment is carried out continuously for no less than 48 hours. In particular, bovine pancreatic deoxyribonuclease (DNase) can be introduced parenterally in doses ranging from 50,000 Kunitz per day to 250,000,000 per day. DNase is an enzyme that catalyzes the hydrolytic cleavage of phosphodiester linkages in the DNA backbone. These doses of DNase are administered anywhere between five and 360 days. In particular, recombinant human DNase (dornase-alpha) can be parenterally introduced in doses ranging from 0.15 mg/day to 500 mg/day between a five-360 day period. The treatment may continue for a life of the patient. Additionally, an agent which bounds extracellular DNA, s.a., anti-DNA antibodies, can also be introduced to the systemic circulation. A modifying agent can further be introduced into the circulation, which modifies the chemical structure, the conformation, the degree of polymerization, or the association of proteins, lipids and/or ribonucleic acids of the blood's extracellular DNA. A preferred modifying agent may be a ribonuclease enzyme and, more particularly, *Serratia Mercenses*.

The present invention suggests that cancer can be treated by reducing circulating DNA levels. Circulating DNA levels are higher in the blood of cancer patients than in healthy controls. Stroun discloses in U.S. Pat. No. 5,952,170 a method of diagnosing cancers, wherein extracellular DNA in the blood is used for diagnostics and for a prognosis of a clinical course of a malignant disease. Hoon and Gocke disclose in U.S. Pat. Nos. 6,465,177 and 6,156,504, respectively, a use of blood's extracellular DNA to define mutations in oncogenes and microsatellic fragments of genes. These patents also disclose usages of blood's extracellular DNA for studying genome instability in tumors.

There is no systematic analysis of blood's extracellular DNA spectrum and its biological role prior to this invention. A search of the prior art reveals no published data concerning a research of blood's extracellular DNA performed without a polymerase chain reaction ("PCR"). Polymerase chain reactions can pervert a pattern of blood's extracellular DNA because of a specificity of primers which are used for amplification. Until recently, a genetic analysis of extracellular blood DNA was mainly carried out by PCR or by blot-hybridization and it was directed to a study of changes in certain fragments of a genome, s.a., e.g., microsatellites and separate genes during a malignant process.

There is thus no available knowledge about a genetic repertoire of blood's extracellular DNA in cancer patients, about a biological role of that blood's extracellular DNA in oncopatology, and about the potential therapeutic effects of a destruction, an inactivation or a treatment of these diseases.

The blood's extracellular DNA in cancer patients contains a unique quantitative and qualitative repertoire of genes and regulating genetic elements which greatly differ from that of DNA in a healthy human genome. In contrast to intracellular DNA, extracellular DNA in cancer patients mainly contains unique human genes, including genes which are involved in a development of and a maintenance of malignant behavior in cancer cells. Because blood's extracellular DNA contributes to malignant growth in cancer patients, a destruction of, a modification of, or a binding of blood's extracellular DNA is useful because it slows down that growth. These interventions are very useful in independent therapy and they also increase an effectiveness of traditional methods of treatment.

The aforesaid new characteristics of this invention are based on new ideas about mechanisms of oncological diseases.

BRIEF DESCRIPTION OF THE DRAWINGS

As set for below the invention has been explained by detailed description of embodiments without references to drawings.

DESCRIPTION OF THE PREFERRED EMBODIMENT

The inventive method is realized as followed:
1. Materials and Methods.
The following agents were used which destroy extracellular blood DNA: bovine pancreatic DNase (Sigma and Samson Med), recombinative human DNase 1 (Dornase alpha; Genetech), *Serratia Mercenses* extracellular nuclease. The solutions of DNase for administration were made by dissolving of mother solutions of DNase in sterile phosphate buffer just before administration.

Extracellular DNA from blood plasma was isolated as follows: fresh plasma (no more than 3-4 hours after sampling) was centrifuged on Ficoll-PlaquePlus (Amersham-Pharmacia) during 20 minutes at 1500 g at room temperature. ½ of plasma was detached, not affecting the rest of cells on the Ficoll pillow, and further centrifuged at 10000 g during 30 min for separation from cell fragments and debris. Supernatant was detached, without affecting the sediment, and was toped up to 1% of sarkosil, 50 mM tris-HCl, pH 7.6, 20 mM EDTA, 400 mM NaCl, and then mixed with equal volume of phenol-chloroform (1:1) mixture. The prepared emulsion was incubated during 2 hours at 65° C., then phenol-chloroform mixture was separated by centrifuging (500 g during 20 minutes, room temperature).

The procedure of deproteinisation with phenol-chlorophorm mixture was repeated 3 times, and then the water phase was processed with chloroform and diethyl ether. Separation from organic solvents was made by centrifugation at 5000 g during 15 minutes). Then equal volume of isopropanol was added to resulting aqueous phase and the mixture was incubated overnight at 0° C. After sedimentation the nucleic acids were separated by centrifugation at 10000 g during 30 minutes. The sediment of nucleic acids was dissolved in 10 mM tris-HCl buffer, pH 7.6 with 5 mM EDTA, and inflicted to the CsCl gradient (1 M, 2.5 M, 5.7 M) in test-tube for rotor SW60Ti. The volume of DNA solution was 2 ml, volume of each step of CsCl was 1 ml. Ultracentrifugation was conducted in L80-80 (Beckman) centrifuge during 3 hours at 250000 g. DNA was collected from the surface of each gradient step into fractions. These fractions were dialyzed during 12 hours (4° C.). Presence of DNA in fractions was determined by agarose electrophoresis and DNA was visualized by ethidium bromide staining. The amount of DNA was determined with specrophotometer (Beckman DU70) in cuvette (100 mkl) at wavelength of 220-230 nm.

Mice Lewis lung carcinoma and Erlich carcinoma were used in experiments. Cells were cultivated in RPMI-1640 medium with 10% calf serum and 1% penicillin-streptomycin in atmosphere of 5% CO2.

For tumor inoculation in mice the cells were cultivated till monolayer is formed, then detached with tripsin-EDTA buffer. The cells were washed 3 times by centrifuging in phosphate buffer and then resuspended up to $0.5 \times 10^7$/ml concentration in the same buffer. The cell viability was determined with methylene blue staining in hemocytometer. Cells suspensions with no less than 95% of living cell were used for transplantation.

C57B1 mice and white randomly bred mice from "Rappolovo" animal house were used. Weight of animals was 24-26 g. 6-7 animals were kept in one cage on a standard diet without limitation of water. LLC cells in dose $5 \times 10^5$ per mice in 0.1 ml of phosphate buffer were transplanted into thigh soft tissues. Erlich tumors were transplanted by administration of 0.2 ml of 10% cell suspension in physiological solution.

In some experiments level of extracellular DNA in blood plasma was quantified. DNA was isolated according to the aforesaid protocol. The DNA level was measured with PicoGreen kit. Electrophoresis of extracellular blood DNA was performed with 1% agarose gel. DNA was visualized with ethidium bromide solution. The levels of high molecular weight DNA fraction (more than 300 base pairs) were determined by densitometry. Lambda phage DNA, digested with EcoRI and HindIII was used as electrophoresis marker.

EXAMPLE 1

Inhibition of Erlich Carcinoma Growth

Recombinant human DNase 1 (Genentech) was used.

1 group: 10 mice bearing Erlich carcinoma were used as control. The mice were injected with 0.2 ml of phosphate buffer intraperitoneally twice a day every day from day 3 to day 7 after the tumor cell transplantation.

2 group: 10 mice bearing Erlich carcinoma were administered intraperitoneal injections of DNase in dose of 1 mg/kg of body weight in 0.2 ml of phosphate buffer four times daily every day from day 3 to day 7 after the tumor cell transplantation.

3 group: 10 mice bearing Erlich carcinoma were administered intraperitoneal injections of DNase in dose of 0.5 mg/kg of body weight in 0.2 ml of phosphate buffer four times daily every day from day 3 to day 7 after the tumor cell transplantation.

4 group: 10 mice bearing Erlich carcinoma were administered intraperitoneal injections of DNase in dose of 0.1 mg/kg of body weight in 0.2 ml of phosphate buffer four times daily every day from day 3 to day 7 after the tumor cell transplantation.

5 group: 10 mice bearing Erlich carcinoma were administered intraperitoneal injections of DNase in dose of 0.05 mg/kg of body weight in 0.2 ml of phosphate buffer four times daily every day from day 3 to day 7 after the tumor cell transplantation. The results were evaluated as tumor Growth Inhibitory Index (GII) (%) at the last day of DNase injections. The quantification of blood plasma extracellular DNA and its electrophoretic qualification were also performed.

The results are presented in Table 1.

Tumor size, extracellular DNA level and extracellular DNA electrophoresis profile on day 7 after tumor transplantation.

TABLE 1

| Group | Tumor volume | Inhibition (%) | Extracellular DNA level, (ng/ml) | Presence of high molecular fractions of extracellular DNA |
|---|---|---|---|---|
| Control | 98 +/− 14 | — | 104.8 | 100%* |
| 1 mg/kg | 23 +/− 6 | 76% | 38.3 | 0 |
| 0.5 mg/kg | 32 +/− 6 | 67% | 55.1 | 25% |
| 0.1 mg/kg | 58 +/− 12 | 37% | 78.0 | 70% |
| 0.05 mg/kg | 87 +/− 11 | 10% | 98.7 | 100% |

*The control group electrophoretic density were considered as 100%.

The presented data demonstrated that sufficiently high doses of DNase 1 are needed to achieve the better therapeutic effect.

EXAMPLE 2

Inhibition of Erlich Carcinoma Growth

Recombinant human DNase I (Genentech) was used.
5 groups of mice bearing LLC were used.
1 group—7 mice—the control.
2 group—6 mice were administered intraperitoneal injections of DNase in dose of 1 mg/kg of body weight twice a day every day from day 3 to day 5 after the tumor cell transplantation.
3 group—6 mice were administered intraperitoneal injections of DNase in dose of 1 mg/kg of body weight twice a day every day from day 3 to day 10 after the tumor cell transplantation.
4 group—6 mice were administered intraperitoneal injections of DNase in dose of 1 mg/kg of body weight twice a day every day from day 3 to day 15 after the tumor cell transplantation.
5 group—6 mice were administered intraperitoneal injections of DNase in dose of 1 mg/kg of body weight twice a day every day from day 3 to day 18 after the tumor cell transplantation.
6 group—6 mice were administered intraperitoneal injections of DNase in dose of 1 mg/kg of body weight twice a day every day on 3,5,7,9,11,13,15 and 17 day after the tumor cell transplantation.
7 group—6 mice were administered intraperitoneal injections of DNase in dose of 0.5 mg/kg of body weight four times daily every day from day 3 to day 10 after the tumor cell transplantation. The results were evaluated as animal survival on day 30 and day 50 after the tumor cell transplantation. The results are presented in Table 2.

Animal survival on day 30 and day 50 after the tumor cell transplantation.

TABLE 2

| Group | day 30 (amount of alive/dead animals in group) | day 50 (amount of alive/dead animals in group) |
|---|---|---|
| 1 | 0-7 | 0-7 |
| 2 | 0-6 | 0-6 |
| 3 | 3-3 | 0-6 |
| 4 | 5-1 | 3-3 |
| 5 | 6-0 | 6-0 |
| 6 | 0-6 | 0-6 |
| 7 | 4-2 | 1-5 |

The presented data demonstrated that the therapy efficacy increases as the treatment time extends. The therapy efficacy is decreased if it is interrupted. Multiple-dose administration is preferred.

EXAMPLE 3

Lung Carcinoma Treatment 54-years-old man has been admitted to the hospital with diagnosis of lung carcinoma.

By patient's agreement, due to lack of any available treatment modality, subcutaneous injections of dornase-alpha were prescribed. The treatment began with administration of daily dose of 50 mkg/kg. Every consecutive day blood extracellular DNA level was measured and blood extracellular DNA was fractioned by electrophoresis. Once a week the primary tumor site and metastases were checked with X-rays and NMR-tomography. After initial 7 day period the dornase-alpha daily dose has been increased up to 100 mkg/kg because of no changes in level and electrophoresis pattern of blood extracellular DNA and no reactions from primary site of the tumor and the metastases. Because of no changes after another 7 days the dosing has been increased up to 150 mkg/kg. Two days after the first injection of the preparation in dose 150 mkg/kg the material recession (more than 50%) of the blood extracellular DNA fraction with the size more than 300 base pairs has been observed although total amount of extracellular DNA has not been greatly decreased (less than 20%). During the next 4 days the patient's general condition has noticeably improved and on day 7 of this cycle of therapy 25%-decreasing of primary tumor lesion size and signs of regression of two bone metastases have been shown by NMR-scanning and X-ray examination. The probes of patient's extracellular DNA taken before the treatment started and 21 days after the beginning the therapy were cloned by means a method which allowed to construct non-amplified plasmid libraries of blood extracellular DNA with representativeness up to one million of clones with the average size of 300-500 base pairs. The DNA which had been isolated with aforesaid protocol was additionally deproteinized with proteinase K (Sigma) at 65° C. for the removal of tightly bound proteins. After the deproteinization and single-stage treatment of phenol-chloroform mixture (65° C.) DNA was precipitated overnight with 2.5 volumes of ethanol. Then DNA was treated by Eco RI restrictase during 3 hours or by Pfu polymerase (Stratagene) in presence of 300 mkM of all desoxynucleotidtriphosphates for sticky-ends elimination. The completed DNA was phosphorylated by polynucleotidkinase T4 (30 U, 2 h.). The preparations were ligated to pBluescript plasmide (Stratagene), which has been digested with EcoRI or PvuII and dephosphorylated by phosphatase CIP (Fermentas) during 1 hour. 1 mkg of vector and 0.1-0.5 mkg of serum DNA were used. The process of ligation was conducted with Rapid Legation Kit (Roche) during 10 hours at 16° C. The volume of this mixture was 50 mkl. The ligated library was transformed into DH12S cells (Life Technologies) by means of electroporator E. Coli porator (BioRad). 12-20 electroporation cuvettes were used for the transformation of one library. The library serial dilutions of $10^{-4}$, $10^{-5}$ and $10^{-6}$ were cloned on 1.5% agar and LB media supplemented with 100 mkg/ml of ampicilline. In both cases the libraries represented $2-3 \times 10^6$ clones.

Analysis of 96 randomly selected clones with the size 300-1000 base pairs from the "before treatment" library showed that 55 from 96 clones were the unique sequences of human DNA. For the 15 sequences from 55 the gene function or corresponding gene product were identified with Human-GeneBank.

| Gene or corresponding protein product | Reported role in cancerogenesis and cancer progression |
|---|---|
| G-protein coupled receptor protein | Key role in neoplastic transformation, apoptosis receptor protein inhibition, hormone independence and metastasis |
| Snf2 coupled CBP activator (SCARP) | Transcription activator, reported in synovial sarcoma and leukemia. |
| SRY-box containing gene | Transcription modulator expressed in embryogenesis. Reported in medulloblastoma, gonadal tumors, highly metastatic melanoma. |
| Tyrosine kinase | Key role in cancer cell regulation network. Some class homologues are the products of cellular oncogenes. |
| Fibroblast activation protein, cell surface protease | Involved into cancer invasion and metastasis. |
| Brain testican | Reported in embryonic rhabdomyosarcoma. |
| KRAB domain, Zn-finger protein. | Reported in early embryogenesis, neuroblastoma, Ewing sarcoma, T-cell lymphoma, linked with acquisition of drug resistance in lung cancer. |
| Melanoma associated antigen | Antigen expressed in melanoma cells. |
| N-cadherin | Involved into cancer invasion and metastasis. |
| Interleukin 7 | Proposed essential autocrine -paracrine growth factor for many cancers |
| DEAD Box RNA helicase-like protein | Expressed in highly proliferating and cancer cells. |
| Lipin-1 | Involved into cancer cell response to cytotoxic drugs. |
| Dynein | Participate in p53 intracellular traffic, reported in prostate cancer and hepatocellular carcinoma. |
| Ramp protein | Reported in human embryonic carcinoma |

Analysis of 100 clones selected randomly from the "21 day after treatment" library showed that more than 90% sequences of clones represented short fragments of repetitive DNA of human genome with dominance of alpha-satellite DNA.

Hence the use of DNAase in doses which are sufficient for destroying extracellular blood DNA with size higher than 300 base pairs leads to disappearing of unique fragments of human genome from extracellular blood DNA, including those involved in development and maintenance of cancer cells malignant behavior. At the same time the tumor responded to applied therapy.

EXAMPLE 4

The Treatment of Malignant Low Differentiated Lymphoma Invading the Spleen and Portal Vien and Metastases in the Liver 49-years-old woman has been admitted to the hospital with the fever (39° C.), progressive jaundice, liver failure and being under suspicion of acute hepatitis suffering. During the inspection malignant lymphoma with the diffusely defeats of spleen and gates of liver and multiply metastases in liver were revealed. By patient's agreement, due to the lack of any specific treatment and because of progression of the disease, intravenous injections of bovine pancreatic DNase were prescribed. Twice a day measuring of level of blood extracellular DNA and its electrophoretic fractioning were conducted. During the first day 500000 units of enzyme were administered as 2 6-hour infusions. Later this dose was increased by 1 000 000 units per day. When the dose was 5500000 units daily the 50% decrease of blood extracellular DNA and disappearance of fraction of DNA with size more than 300 base pairs were noted. As the continued DNA infusions at 5500000 units per day were being performed the patient's general condition was being improved, fever and jaundice disappeared, biochemical indexes of blood taken a turn to the better. Control Doppler examination which has been made at day 20 after the beginning of the treatment showed significant reduction (more than 40%) of lesion in the spleen and disappearance of more than half of all metastatic sites in the liver. The woman was moved to another hospital for conducting chemotherapy.

Hence the use of DNase in doses which are sufficient for destroying extracellular DNA of blood with size higher than 300 base pairs leads to tumor regression according to the inventive method.

EXAMPLE 5

The Study of Influence of Polyclonal Serum Containing the Antibodies Against DNA on the Growth of Erlich Carcinoma of in Mice Treating with DNAase Antibodies against DNA were isolated from the blood of patients with systemic lupus erythematosus according to method of Shuster. A. M. (Shuster A. M. et. al., Science, v.256, 1992, pp. 665-667). Such anti-DNA antibodies could not only bind DNA but also hydrolyze it. Human recombinant DNase 1 (Genetech) was used.

1 group—7 mice bearing Erlich carcinoma—control.

2 group—6 mice bearing Erlich carcinoma received intravenous injection of human anti-DNA antibodies (Ig G) in dose of 200 mkg per animal on day 3 after the carcinoma transpalantation. Mice also have been administered with DNase in dose 0.5 mg/kg 4 times intraperitonealy a day from day 3 to day 7 after the tumor transplantation.

3 group—6 mice bearing Erlich carcinoma received intravenous injection of human non-specific immunoglobulin (IgG) in dose of 200 mkg per animal on day 3 after the carcinoma transpalantation. Mice also have been administered with DNAase in dose 0.5 mg/kg 4 times intraperitonealy a day from day 3 to day 7 after the tumor transplantation.

4 group—6 mice bearing Erlich carcinoma received intravenous injection of human DNase in dose of 0.5 mg/kg 4 times intraperitonealy a day from day 3 to day 7 after the tumor transplantation.

The effect was evaluated as the tumor growth inhibition on day 7 after the tumor cell transplantation (TGI, evaluated in percent). The results are presented in Table 3.

The tumor volume on day 7 after tumor transplantation.

TABLE 3

| Group | Tumor volume | T % |
|---|---|---|
| 1 | 105 +/− 12 | — |
| 2 | 25 +/− 5 | ~75% |
| 3 | 37 +/− 6 | ~66% |
| 4 | 35 +/− 7 | ~67% |

The presented data demonstrated that the combined therapy with DNase and the agent binding blood exracellular DNA has more noticeable antitumor effect.

EXAMPLE 6

The Study of Degradation Kinetics of High Molecular Weight Fraction (Size more than 300 Pairs of Bases) of Blood Extracellular DNA of Breast Cancer Patient in the Presence of Bovine Pancreatic DNase, Proteinase K and Bovine Pancreatic DNase, Lipase and Bovine Pancreatic DNase and Extracellular Desoxyrybonuclease *Serratia Mercenses*, which has Ribonuclease Activity and is as Destroyed and Modifying Agent at the Same Time The respective enzyme was added to a sample of patient's plasma and incubated for 45 minutes at 37° C. 45 minutes later the reaction has being stopped and isolation and electrophoretic fractioning with densitometry of blood extracellular DNA have being performed.

The results are presented in Table 4.

Degradation kinetics of high molecular fraction.

TABLE 4

| The way of working | Degradation of high molecular fraction, % |
|---|---|
| Intact control | 0 |
| Proteinase K (0.1 mkg/ml) | 0 |
| Pancreatic lipase (0.1 mkg/ml) | 0 |

TABLE 4-continued

| The way of working | Degradation of high molecular fraction, % |
|---|---|
| Bovine pancreatic DNAase (1 Kuntz Units/ml) | 25 |
| Bovine pancreatic DNAase (1 Kuntz Units\ml) + proteinase K (0.1 mkg\ml) | 35 |
| Bovine pancreatic DNAase (1 Kuntz Units/ml) + pancreatic lipase (0.1 mkg/ml) | 40 |
| Extracellular desoxyribonuclease of *Serratia Mercenses* (1 Kuntz Units/ml) | 45 |

The presented data demonstrated that the combined therapy with DNase and the agent modifying blood exracellular DNA binding with proteins, lipids and ribonucleic acids leads to more effective degradation of high molecular fraction (size more than 300 pairs of bases) of blood extracellular DNA.

EXAMPLE 7

The Study of the Influence of Different Methods of Destroying Extracellular DNA on its Pathogenic Properties C57B1 mice have been inoculated with high metastatic or low metastatic strain of LLC tumor. On the 9th day after the inoculation animals were euthanized and pool of their blood plasma was collected. The summary fraction of extracellular blood plasma DNA was kept in phosphate butler at −20° C.

7 groups of mice inoculated with low metastatic strain of LLC were included in the experiment.

1 group—6 mice grafted by low metastatic LLC strain.

2 group—6 mice grafted by low metastatic LLC strain and were subjected to twice repeated intravenous administration (on 7 and 8 day after inoculation) of summary fraction of extracellular DNA from mice grafted by high metastatic strain (before the administration 0.05 mkg of DNA have been dissolved in 500 mkl of fresh heparinized blood).

3 group—6 mice grafted by low metastatic LLC strain and were subjected to twice repeated intravenous administration (on 7 and 8 day after inoculation) of summary fraction of extracellular DNA from mice grafted by high metastatic strain (before the administration 0.05 mkg of DNA have been dissolved in 500 mkl of fresh heparinized blood). Before the administration the sample with DNA has been disinfected photochemically (by adding 1 mkM of methylene blue stain and exposure of red light during 10 min (~60 000 lux).

4 group—6 mice grafted by low metastatic LLC strain and were subjected to twice repeated intravenous administration (on 7 and 8 day after inoculation) of summary fraction of extracellular DNA from mice grafted by high metastatic strain (before the administration 0.05 mkg of DNA have been dissolved in 500 mkl of fresh heparinized blood). Before the administration the sample with DNA has been mixed with 10 mkg of hydrolytic anti-DNA antibodies.

5 group—6 mice grafted by low metastatic LLC strain and were subjected to twice repeated intravenous administration (on 7 and 8 day after inoculation) of summary fraction of extracellular DNA of mice graft by high metastatic strain (before the administration 0.05 mkg of DNA have been dissolved in 500 mkl of fresh heparinized blood). Before the administration 1 mkg of the fragment A of the plant toxin Ricin was added to the sample and the mixture was incubated during 1 hour at 37° C. Ricin is the representative of RIP-toxins family (proteins inactivating ribosomes) which widely used for immunotoxins' development. In addition to its capability to inactivate ribosomes these proteins also can deadenilate and hydrolyze DNA. To realize the toxic effect the unit A of the type II RIP toxin should be delivered into cell by unit B. In the absence of subunit B chain A is not toxic, however polyadeninglicosidase activity of chain A can be used for destruction of DNA circulating in blood.

6 group—6 mice grafted by low metastatic LLC strain were subjected to twice repeated intravenous administration (on 7 and 8 day after inoculation) of summary fraction of extracellular DNA from mice grafted by high metastatic strain (before the administration 0.05 mkg of DNA have been dissolved in 500 mkl of fresh heparinized blood). The DNA sample was enzymatically methylated before the administration. (I. Muiznieks et. al., FEBS Letters, 1994, v. 344,pp.251-254).

7 group—6 mice grafted by low metastatic LLC strain were subjected to twice repeated intravenous administration (on 7 and 8 day after inoculation) of summary fraction of extracellular DNA of mice graft by low metastatic strain 8 group—6 mice grafted by low metastatic LLC strain were subjected to twice repeated intravenous administration (on 7 and 8 day after inoculation) of summary fraction of extracellular DNA of mice grafted by high metastatic strain (before the administration 0.05 mkg of DNA have been dissolved in 500 mkl of fresh heparinized blood). The sample with DNA was incubated with 200 ng/ml of dornase alpha during 30 minutes at 37° C. before the administration.

The number of lung metastases (N cp) was evaluated on day 15 after the inoculation.

The results are presented in Table 5.

The number of lung metastases on day 15 after the tumor inoculation subject to the extracellular DNA destruction method.

TABLE 5

| Group | N cp |
|---|---|
| 1 | 12.0 |
| 2 | 22.5 |
| 3 | 14.1 |
| 4 | 15.5 |
| 5 | 15.1 |
| 6 | 12.3 |
| 7 | 13.3 |
| 8 | 13.5 |

Hence blood extracellular DNA of mice bearing highly malignant tumor strain increases metastasis of less malignant tumor. Destruction, binding and modification of blood extracellular DNA suppress that process according to the inventive method.

EXAMPLE 8

Pilot Clinical Trials of DNase Enzyme Monotherapy in Patients with Advanced Cancer of Different Origin The trials were performed in St. Petersburg Academy of Advanced Medical Education; Department of Thoracic Surgery. Total 12 patients were included according to following inclusion criteria:

Men and women 18 y. or older
T4M+ advanced cancer of any orign
Diagnosis proved by clinical, instrumental and laboratory assessment
Absence of any alternative treatment modality
CT (Spiral Computer Tomography) or clinical evidence of rapidly progressing disease
Karnofsky performance score >40
The following patients were included:
MOI—Malignant Melanoma. Multiple lung and liver metastasis.
GEF—Breast cancer. Disseminated bone metastasis.
FVV—Breast cancer. Disseminated lung and liver metastasis.
KNP—Gastric cancer. Disseminated lymphatic and liver metastasis.
PGP—Colon cancer. Disseminated lung and liver metastasis.
MCF—Colon cancer. Local reappearance. Disseminated lymphatic and liver metastasis.
MVI—Pancreatic adenocarcinoma. Disseminated lymphatic metastasis.
SSA—Lung cancer. Disseminated lung and lymphatic metastasis.
ISP—Colon cancer. Liver metastasis.
BVI—Recurrent Renal cancer. Multiply bone metastasis.
CLV—Recurrent rectal carcinoma. Multiply bone and lung metastasis.
BAI—Lung cancer. Disseminated lung and lymphatic metastasis The patients received one course of monotherapy with bovine pancreatic DNase enzyme according following regimen:
Treatment duration—21 day.
DNase delivery—20 min. intravenous infusion in isotonic sodium chloride.
Number of daily infusions—6.
Day 1-8: 50 mg per infusion (510 000 Kunitz units per day)
Day 8-12: 75 mg per infusion (765 000 Kunitz units per day)
Day 12-21: 100 mg per infusion (1 020 000 Kunitz units per day)

The efficacy was assessed on day 30 after start of therapy. All patients demonstrated stabilization of the disease. (Spiral CT scan; RECIST criteria). All patients demonstrated significant increase in Karnofsky performance score; some patients showed shrinkage of metastatic nodules. It can be therefore concluded that DNase therapy is effective in treatment of malignant tumors of different origin. In Terms of Different DNase Enzymes:

EXAMPLE 9

Inhibition of Growth of Human Tumors in Nude Mice Under Treatment with Different High-dose DNase Enzymes DNase IIβ DLAD is an enzyme that degrades DNA during lens cell differentiation and was purchased from Abnova Corporation. DNase 1L1 is a member of deoxyribonuclease family showing high sequence similarity to lysosomal DNase I (Abnova Corporation). TURBO™ DNase is genetically reengineered form of bovine DNase I for greater catalytic efficiency than conventional DNase I at higher salt concentrations and lower DNA concentrations. The enzyme was purchased from Ambion.

All experiments were performed in 6-8 week old female nu/nu mice. Eighty eight nude mice were randomly divided into control and experimental groups as follows:

| Group | Animals per group | Tumor | DNASE enzyme | Dosage | %% of Tumor growth inhibition |
|---|---|---|---|---|---|
| 1 | 8 | COLO205 | Saline | — | 0% |
| 2 | 6 | COLO205 | DNASE DLAD | 5 mkg\kg | 0% |
| 3 | 6 | COLO205 | DNASE DLAD | 250 mkg\kg | 60% |
| 4 | 6 | COLO205 | TURBO DNASE | 5 U\kg | 5% |
| 5 | 6 | COLO205 | TURBO DNASE | 500 U\kg | 75% |
| 6 | 6 | COLO205 | DNASE 1L1 | 5 mkg\kg | 0% |
| 7 | 6 | COLO205 | DNASE 1L1 | 250 mkg\kg | 100% |
| 8 | 8 | NCI-H82 | Saline | — | 0% |
| 9 | 6 | NCI-H82 | DNASE DLAD | 5 mkg\kg | 0% |
| 10 | 6 | NCI-H82 | DNASE DLAD | 250 mkg\kg | 50% |
| 11 | 6 | NCI-H82 | TURBO DNASE | 5 U\kg | 10% |
| 12 | 6 | NCI-H82 | TURBO DNASE | 500 U\kg | 75% |
| 13 | 6 | NCI-H82 | DNASE 1L1 | 5 mkg\kg | 10% |
| 14 | 6 | NCI-H82 | DNASE 1L1 | 250 mkg\kg | 90% |

COLO205 (Human colon cancer) and NC1-H82 (Human lung cancer) cells (10-to-12 million) were injected s.c. in the left flank of animals. Once a palpable tumor was observed seven daily intramuscular injections of DNase enzyme or saline were given as indicated in the table above. The anti-tumor activity following DNase treatment was assessed by measuring the tumor dimensions at the day following the day of last injection in the control (PBS) and DNase-treated groups. The apparent tumor volume was calculated using the formula [tumor volume (mm$^3$)=(Length×Width$^2$)/2]. The results of treatment expressed as % % of tumor growth inhibition in DNase-treated animals in comparison with controls arc presented in the above table. Thus, different DNase enzymes possess anti-cancer activity at doses used.

The foregoing descriptions of specific embodiments of the present invention have been presented for purposes of illustration and description. They are neither intended to be exhaustive nor to limit the invention to the precise forms disclosed and, obviously, many modifications and variations are possible in light of the above teaching. The embodiments were chosen and described in order to best explain the principles of the invention and its practical application, to thereby enable others skilled in the art to best utilize the invention and its various embodiments with various modifications as are suited to the particular use contemplated. It is intended that the scope of the invention be defined by the Claims appended hereto and their equivalents. Therefore, the scope of the invention is to be limited only by the following claims.

Having this described the invention, what is claimed as new and desired to be secured by Letters Patent is as follows:

1. A method of treating a cancer in a patient in need thereof, wherein the cancer is accompanied with elevation of blood extracellular DNA level, said method comprising parenterally administering to the patient a DNase enzyme in doses and regiments which provide blood plasma DNA-hydrolytic activity to exceed 150 Kunitz units per liter of plasma during more than 12 hours within 24 hours, and further comprising parenterally administering to said patient an anti-DNA antibody.

2. A method of treating a cancer in a patient in need thereof, wherein said cancer is malignant melanoma and is accompanied with elevation of blood extracellular DNA level, said method comprising parenterally administering to the patient a DNase enzyme in doses and regiments which provide blood plasma DNA-hydrolytic activity to exceed 150 Kunitz units per liter of plasma during more than 12 hours within 24 hours.

3. The method according to claim 2, wherein the DNase enzyme is human recombinant DNase.

4. The method according to claim 1, wherein the DNase enzyme is human recombinant DNase.

* * * * *